(12) United States Patent
Vogt et al.

(10) Patent No.: US 8,596,499 B2
(45) Date of Patent: Dec. 3, 2013

(54) CARTRIDGE SYSTEM WITH ROTATABLE CLOSURE AND DISPENSING TUBE

(75) Inventors: Sebastian Vogt, Erfurt (DE); Hubert Büchner, Nürnberg (DE); Tim Schnieber, Frankfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 180 days.

(21) Appl. No.: 13/096,233

(22) Filed: Apr. 28, 2011

(65) Prior Publication Data

US 2011/0272434 A1    Nov. 10, 2011

(30) Foreign Application Priority Data

May 4, 2010    (DE) .......................... 10 2010 019 219

(51) Int. Cl.
| | |
|---|---|
| *B67D 7/70* | (2010.01) |
| *B67D 7/78* | (2010.01) |
| *B67D 3/00* | (2006.01) |
| *B67D 7/06* | (2010.01) |
| *B65D 35/54* | (2006.01) |
| *B65D 88/54* | (2006.01) |
| *B65D 47/20* | (2006.01) |
| *G01F 11/00* | (2006.01) |
| *A61C 5/04* | (2006.01) |

(52) U.S. Cl.
USPC .......... 222/137; 222/96; 222/145.6; 222/326; 222/506; 222/536; 433/90

(58) Field of Classification Search
USPC ............ 222/137, 145.1, 145.4–145.6, 92–94, 222/252, 326, 505–506, 531–533, 556, 561, 222/568; 433/89–90; 251/289–299, 315.06
See application file for complete search history.

(56) References Cited

U.S. PATENT DOCUMENTS

| | | |
|---|---|---|
| 1,092,433 A | 4/1914 | Cox |
| 1,308,091 A | 7/1919 | Maurer |

(Continued)

FOREIGN PATENT DOCUMENTS

| | | |
|---|---|---|
| AU | 653201 B2 | 9/1994 |
| CH | 669164 A5 | 2/1989 |

(Continued)

OTHER PUBLICATIONS

European Search Report Dated September 13, 2011 for EP 11 00 3139 corresponding to present application.

(Continued)

*Primary Examiner* — Paul R Durand
*Assistant Examiner* — Matthew Lembo
(74) *Attorney, Agent, or Firm* — Norris McLaughlin & Marcus, P.A.

(57) ABSTRACT

Cartridge systems for application of a material have at least one cartridge having cartridge walls, a cartridge head having at least one opening in the cartridge head, and a bracket arranged on the cartridge head. A valve is mounted in rotatable manner in the bracket and has at least one passage through the valve that is connected to an outlet opening of the valve. In a closed position, the valve closes the at least one opening of at least one cartridge in a sealed manner. The at least one passage of the valve is connected to the at least one opening when the valve is located in an open position such that the cartridge content is squeezable out of the at least one cartridge through the outlet opening, and further wherein the valve is configured to be transitioned from a closed position to an open position through a rotation of the valve about an axis of symmetry of the valve.

18 Claims, 8 Drawing Sheets

(56) References Cited

U.S. PATENT DOCUMENTS

| | | | |
|---|---|---|---|
| 1,920,165 A | 8/1933 | Andvig | |
| 2,125,245 A | 7/1938 | McCray | |
| 2,446,501 A | 8/1948 | Weber | |
| 2,694,506 A | 11/1954 | Knapp | |
| 2,818,899 A | 1/1958 | De Back | |
| 2,973,885 A | 3/1961 | Ferguson | |
| 3,116,856 A * | 1/1964 | Prussin et al. | 222/402.24 |
| 3,215,298 A | 11/1965 | Shaffer | |
| 3,570,719 A | 3/1971 | Schiff | |
| 3,752,368 A | 8/1973 | Robertson | |
| 3,768,472 A | 10/1973 | Hodosh et al. | |
| 3,834,433 A | 9/1974 | Thompson | |
| 3,938,709 A | 2/1976 | Collar | |
| 3,983,947 A | 10/1976 | Wills et al. | |
| 4,068,830 A | 1/1978 | Gray | |
| 4,318,403 A * | 3/1982 | Sneider | 604/2 |
| 4,386,717 A | 6/1983 | Koob | |
| 4,432,469 A | 2/1984 | Eble et al. | |
| 4,441,629 A | 4/1984 | Mackal | |
| 4,690,306 A | 9/1987 | Staheli | |
| 4,846,373 A * | 7/1989 | Penn et al. | 222/137 |
| 4,848,598 A * | 7/1989 | McKinney | 222/391 |
| 4,871,088 A | 10/1989 | Cox | |
| 4,925,061 A | 5/1990 | Jeromson, Jr. et al. | |
| 4,967,797 A | 11/1990 | Manska | |
| 4,981,241 A | 1/1991 | Keller | |
| 4,989,758 A | 2/1991 | Keller | |
| 5,027,981 A * | 7/1991 | Magister | 222/137 |
| 5,072,862 A | 12/1991 | Keller | |
| 5,080,262 A | 1/1992 | Herold et al. | |
| 5,137,182 A | 8/1992 | Keller | |
| 5,156,421 A | 10/1992 | Chauvel | |
| 5,301,631 A | 4/1994 | Vining | |
| 5,301,842 A | 4/1994 | Ritter | |
| 5,441,175 A | 8/1995 | Jacobsen et al. | |
| 5,443,182 A | 8/1995 | Tanaka et al. | |
| 5,477,987 A | 12/1995 | Keller | |
| 5,498,078 A | 3/1996 | Keller | |
| 5,514,135 A | 5/1996 | Earle | |
| 5,566,860 A * | 10/1996 | Schiltz et al. | 222/94 |
| 5,667,102 A | 9/1997 | Keller | |
| 5,890,628 A * | 4/1999 | Simpson et al. | 222/131 |
| 5,893,486 A | 4/1999 | Wasmire | |
| 5,894,869 A | 4/1999 | Mussack | |
| 5,944,226 A * | 8/1999 | Schiltz et al. | 222/137 |
| 5,968,018 A | 10/1999 | Freeman et al. | |
| 6,029,857 A | 2/2000 | Keller | |
| 6,077,138 A | 6/2000 | Schulze | |
| 6,296,149 B1 | 10/2001 | Long | |
| 6,311,871 B1 | 11/2001 | Binder | |
| 6,547,101 B1 | 4/2003 | Sogaro | |
| 6,783,509 B1 | 8/2004 | Landau et al. | |
| 6,935,541 B1 | 8/2005 | Campbell et al. | |
| 7,163,130 B2 | 1/2007 | Lafond | |
| 7,185,792 B2 | 3/2007 | Gibbons et al. | |
| 7,188,753 B2 | 3/2007 | Campbell | |
| 7,481,333 B2 * | 1/2009 | Goldberg et al. | 222/135 |
| 7,530,808 B2 * | 5/2009 | Cao et al. | 433/89 |
| 7,637,398 B2 | 12/2009 | Sung | |
| 7,677,418 B2 | 3/2010 | Henniges et al. | |
| 7,752,974 B2 | 7/2010 | Wenaas et al. | |
| 7,845,517 B2 | 12/2010 | Py et al. | |
| 7,963,937 B2 * | 6/2011 | Pauser et al. | 604/82 |
| 8,016,161 B2 * | 9/2011 | Pierson et al. | 222/137 |
| 8,028,858 B2 | 10/2011 | Hollars | |
| 8,177,099 B2 * | 5/2012 | Suchan et al. | 222/137 |
| 8,292,619 B2 | 10/2012 | Peuker et al. | |
| 8,328,553 B2 * | 12/2012 | Broyles et al. | 433/90 |
| 2001/0008968 A1 | 7/2001 | Overes et al. | |
| 2002/0052579 A1 | 5/2002 | Sogaro | |
| 2002/0188250 A1 | 12/2002 | Landau et al. | |
| 2003/0179648 A1 | 9/2003 | Heusser et al. | |
| 2004/0074927 A1 | 4/2004 | Lafond | |
| 2004/0104249 A1 | 6/2004 | Horth et al. | |
| 2004/0216591 A1 | 11/2004 | Assadi et al. | |
| 2005/0150916 A1 | 7/2005 | De Laforcade | |
| 2005/0230433 A1 | 10/2005 | Campbell | |
| 2005/0241703 A1 | 11/2005 | Takacs | |
| 2005/0247740 A1 | 11/2005 | Puzio | |
| 2005/0269368 A1 | 12/2005 | Proulx | |
| 2006/0208000 A1 | 9/2006 | Murray et al. | |
| 2007/0051750 A1 | 3/2007 | Suchan et al. | |
| 2007/0164047 A1 * | 7/2007 | Reidt et al. | 222/137 |
| 2007/0175921 A1 | 8/2007 | Keller | |
| 2008/0086079 A1 | 4/2008 | Williamson et al. | |
| 2008/0210708 A1 | 9/2008 | Yeames | |
| 2008/0247262 A1 | 10/2008 | Henniges et al. | |
| 2008/0287880 A1 | 11/2008 | Keller | |
| 2008/0304355 A1 | 12/2008 | Sattig et al. | |
| 2008/0314929 A1 | 12/2008 | Keller | |
| 2009/0057338 A1 * | 3/2009 | Knee et al. | 222/94 |
| 2009/0062808 A1 | 3/2009 | Wolf, II | |
| 2009/0065532 A1 | 3/2009 | Lafond | |
| 2009/0071459 A1 | 3/2009 | Wenaas et al. | |
| 2009/0105144 A1 | 4/2009 | Vogt et al. | |
| 2009/0105366 A1 | 4/2009 | Vogt et al. | |
| 2010/0200618 A1 | 8/2010 | Dubach | |
| 2010/0319796 A1 | 12/2010 | Whitaker | |
| 2011/0272436 A1 | 11/2011 | Vogt et al. | |
| 2011/0272438 A1 | 11/2011 | Vogt et al. | |

FOREIGN PATENT DOCUMENTS

| | | |
|---|---|---|
| DE | 2017292 A1 | 10/1971 |
| DE | 3440893 A1 | 5/1986 |
| DE | 3530212 C1 | 10/1986 |
| DE | 91 02 635 U1 | 5/1991 |
| DE | 9102635 U1 | 5/1991 |
| DE | 297 09 383 U1 | 10/1998 |
| DE | 20107507 U1 | 3/2002 |
| DE | 20 2006 014087 U1 | 12/2006 |
| DE | 102005041961 A1 | 3/2007 |
| DE | 102006001056 A1 | 7/2007 |
| DE | 202006015457 U1 | 2/2008 |
| DE | 20 2008 009692 U1 | 10/2008 |
| DE | 102007044983 A1 | 4/2009 |
| DE | 102007052116 A1 | 4/2009 |
| DE | 102007050762 A1 | 5/2009 |
| DE | 202005010206 | 9/2009 |
| DE | 102008030312 A1 | 1/2010 |
| EP | 0028032 A1 | 5/1981 |
| EP | 0169533 A2 | 1/1986 |
| EP | 0213073 A1 | 3/1987 |
| EP | 0236129 A2 | 9/1987 |
| EP | 0261466 A1 | 3/1988 |
| EP | 0289882 A1 | 11/1988 |
| EP | 0294672 | 12/1988 |
| EP | 0431347 | 6/1991 |
| EP | 0607102 A1 | 7/1994 |
| EP | 0664153 A1 | 7/1995 |
| EP | 0693437 A1 | 1/1996 |
| EP | 0787535 A1 | 8/1997 |
| EP | 1118313 | 7/2001 |
| EP | 2008707 | 12/2008 |
| FR | 650 157 A | 1/1929 |
| GB | 1188516 A1 | 4/1970 |
| GB | 2195713 A | 4/1988 |
| JP | 2003341749 A | 12/2003 |
| JP | 2005289470 A | 10/2005 |
| JP | 2009529377 A | 8/2009 |
| JP | 2009 291234 A | 12/2009 |
| WO | 2006005206 A1 | 1/2006 |
| WO | 2008100130 A2 | 8/2008 |
| WO | 2008109439 | 9/2008 |
| WO | 2009036962 A2 | 3/2009 |
| WO | 2009/061884 A1 | 5/2009 |
| WO | 2010006455 A1 | 1/2010 |

OTHER PUBLICATIONS

European Search Report Dated September 15, 2011 for EP 11 00 3130, corresponding to U.S. Appl. No. 13/096,105.
"Australian Search Report dated Jul. 28, 2012 for AU Application No. 2011201857 corresponding to related U.S. Appl. No. 13/096,260."

(56) References Cited

OTHER PUBLICATIONS

Canadian Intellectual Property Office, Office Action dated Aug. 1, 2012.
Australian Search Report for related AU 2011202037, mailed Aug. 16, 2012.
Computer-generated, English-Language Translation of Japanese Office Action for related Japanese Application No. 2011-103859 dated Jan. 25, 2013.
Chinese Office Action for co-pending U.S. Appl. No. 13/096,156 for related Chinese Application No. 201110113264.4 dated Feb. 4, 2013.
Non-Final Rejection from related U.S. Appl. No. 13/096,260, mailed Jul. 10, 2013.
Notice of Allowance from related U.S. Appl. No. 13/096,156, mailed Aug. 26, 2013.
Final Rejection from related U.S. Appl. No. 13/096,105, mailed Aug. 28, 2013.
Non-Final Rejection from related U.S. Appl. No. 13/096,062, mailed Sep. 5, 2013.
Japanese Office Action for corresponding JP Application No. 2011-103862 dated Jul. 29, 2013 with English-Language Translation.

\* cited by examiner

CARTRIDGE SYSTEM WITH ROTATABLE CLOSURE AND DISPENSING TUBE

The invention relates to a cartridge system for application of a material, in particular a medical cement, comprising at least one cartridge, whereby the at least one cartridge comprises cartridge walls and one cartridge head each having at least one opening in each cartridge head, and a bracket is arranged on the cartridge head or cartridge heads.

BACKGROUND OF THE INVENTION

Reactive pasty two- or multi-component systems must be stored separately after their production and until their application in order to prevent premature, inadvertent reactions of the components. Cartridge systems for the application of pasty two- or multi-component systems have been known for decades. The following documents are cited for exemplary purposes, CH 669 164 A5, EP 0 607 102 A1, EP 0 236 129 A2, DE 3 440 893 A1, U.S. Pat. No. 4,690,306 A, US 2009/062808 A1, EP 0 787 535 A1, WO 2006/005 206 A1, EP 0 693 437 A1, EP 0 294 672 A, EP 0 261 466 A1, and EP 2 008 707 A1. After the cartridges are filled with reactive pastes, the cartridges need to remain safely closed until their application. The pasty two- or multi-component systems are mixed right before their application, usually through the use of static mixers. In this context, the following documents are cited for exemplary purposes, GB 1,188,516 A, U.S. Pat. No. 2,125, 245 A, U.S. Pat. No. 5,968,018 A, U.S. Pat. No. 4,068,830 A, US 2003/179648 A1, EP 0 664 153 A1, and EP 0 289 882 A1. In this context, mobile plungers seal the cartridge floors and are subsequently used to squeeze out the pastes during their application. A cartridge system having a snap-in locking device on a feed plunger of a cartridge is known from EP 2 008 707 A1.

A number of solutions has been proposed for closing a cartridge head.

One simple, but very effective, principle is to close the cartridge head with a closure that can be rotated (EP 0 431 347 A1, DE 2 017 292 A1, U.S. Pat. No. 3,215,298 A). The closure is unscrewed prior to the application. Subsequently, a dispensing tube is screwed into a thread on the cartridge head or fixed through a peg system that simulates a thread. This is disadvantageous in that the user needs to perform rotational motions twice until the paste material can be expelled. Moreover, the closure may be screwed out and the dispensing tube is attached only later. In the interim between the cartridges being opened and the dispensing tube being inserted, ingredients of the pastes may evaporate, especially if the pastes contain volatile substances.

The closure that is in very common use currently in the adhesives and sealant industry is based on the wall material of the cartridge being provided to be very thin at the cartridge head such that said wall can be perforated easily. It is disadvantageous that the perforation might be associated with particles detaching from the wall and then entering the pasty material.

Polymethylmethacrylate bone cements have been in use in medicine for decades for permanent mechanical fixation of total joint endoprostheses. They are based on powder-liquid systems. Recently, polymethylmethacrylate bone cements that are based on the use of cement pastes have been proposed as well (DE 10 2007 050 762 A1, DE 10 2008 030 312 A1, DE 10 2007 052 116 A1). Thus far, no suitable cartridge systems have been proposed for said cements.

With regard to the application of bone cements for fixation of total joint endoprostheses, it is always necessary to take into consideration that the OR staff is under time pressure during these surgeries. Therefore, as a matter of principle, cartridge systems for medical applications involving the application of paste-like polymethylmethacrylate bone cements should be designed such that they are largely resistant to user errors and can be operated rapidly and safely even in stressful situations.

The methylmethacrylate monomer is an essential ingredient of paste-like polymethylmethacrylate bone cements. Said monomer evaporates readily and has a relatively high vapour pressure at room temperature. For this reason, it is essential to note with regard to the use of methylmethacrylate-containing pastes that the cartridge plungers in the cartridges may be moved and may be expelled from the cartridges in the extreme case by the evaporating methylmethacrylate upon exposure to a vacuum, such as during the de-gassing as part of ethylene oxide sterilisation.

A cartridge system that is based on packaging pasty multi-component systems in tubular bags is known from WO 2010/006455 A1. This involves inserting the sealed tubular bags into cartridges. Tubular bags are advantageous in that they are suitable for packaging pastes that contain volatile ingredients. Tubular bags made of compound materials, such as aluminium compound bags, are particularly well-suited for this purpose. The tubular bags are opened by blades that rotate along when the dispensing tube is being screwed in. The bags are cut open in the course of the rotational motion of the blades and openings in the cartridges for dispensing the content are thus provided. The pasty bag content is subsequently squeezed or pressed through these openings in the cartridges in the direction of the static mixer.

In this context, it is disadvantageous that packaging pasty materials in tubular bags and, in addition, in cartridges is quite expensive and reserved for special applications only. Moreover, it is a problem in many applications, especially in the field of medicine, that parts of the cut tubular bags may become detached and thus may enter into the pasty components and thus contaminate the mixing ware.

A cartridge system of this type is known from EP 0 431 347 A1. The system provides openings on the cartridge heads of two cartridges through which the cartridge content can be expelled. A closure that is fastened to a bracket on the cartridge heads closes the openings.

This is disadvantageous in that the closure not only is plugged into the openings, but also snapped-in in the bracket such that removing the closure requires an effort to be made. Moreover, removed from the cartridge system, the closure may get in the way or, in case it is to be used to re-close the openings, it may get lost.

SUMMARY OF THE INVENTION

It is therefore the object of the invention to develop a simple, inexpensive closure system for cartridge systems that reduces or overcomes the shortcomings of the traditional cartridge closure systems. Accordingly, a cartridge closure system is to be developed that safely closes cartridges and allows the individual cartridges to be opened rapidly and without difficulties while being easy to handle. Moreover, only a minimal number of working steps should be required to attach a dispensing tube to the cartridge head or cartridge heads in the dispensing position in order to prevent operating errors of the user. Contamination of the dispensed flowable material in the process should be prevented.

The object is met in that a valve is mounted in rotatable manner in the bracket, whereby the valve comprises at least one passage through the valve that is connected to an outlet opening, in that the valve, in a closed position, closes at least one opening of at least one cartridge, in particular all openings of all cartridges, in a sealed manner, in that the passage or passages is or are connected to the opening or openings in an open position of the valve such that the cartridge content can be squeezed out of the cartridge or cartridges through the outlet opening, and whereby the valve can be transitioned from the closed position to the open position through a rotation of the valve.

In this context, the invention can provide each cartridge to comprise at least one feed plunger opposite from the cartridge head for expelling the cartridge content through the opening, which feed plunger closes the cartridge or cartridge on the floor side, in particular in a gas-tight manner.

The invention can also provide the content of the cartridge or cartridges to be a flowable material.

Moreover, the invention can provide at least one sealing ring in the valve on one or more opening or openings such that, with the valve being open, at least one fluid-tight connection from the opening in the cartridge or the openings in the cartridges to the passage or passages is or are provided.

Moreover, the invention proposes a connector to be arranged on the valve, whereby the connector comprises a fastening means for fastening a dispensing tube, the passage extends through the connector, and the outlet opening is arranged on the connector.

In this context, the invention can provide the fastening means to be a thread, in particular an external thread.

Moreover, to further simplify the operation, the invention is to provide a cartridge system having the cartridge closure system to be developed that safely prevents any motion of the plungers upon the action of a vacuum. Moreover, the multi-component cartridge system is to facilitate synchronous motion of the plungers in the cartridges upon the action of a force in the direction of the cartridge head, and thus squeeze-out the flowable materials evenly such that the mixing ratio of the flowable materials with respect to each other is ensured.

Accordingly, a particularly advantageous cartridge system can be implemented in that a mobile rod is arranged, parallel to the at least one cartridge, preferably between at least two cartridges, particularly preferably in a hollow body about which multiple cartridges are arranged to be parallel, parallel to the feed plungers and fixedly connected to the feed plungers through at least a fin and/or a plate, whereby the rod comprises a snap-in locking means on the side facing the valve, and an opposite snap-in locking means is attached at the cartridge wall or cartridge walls or preferably on the internal wall of the hollow body, and acts in concert with the snap-in locking means of the rod in a manner such that a motion of the rod in the direction of the cartridge floor and therefore a motion of the feed plungers out of the cartridges is significantly hampered, in particular is prevented.

Moreover, the invention can provide the cartridge wall or cartridge walls to include at least one slit that commences at the cartridge floor and is arranged parallel to the rod, whereby the width of the slit or slits is sufficient to take up the fin or fins and, in particular, the length of the slit or slits extends, in particular, to at least half of the length of the cartridge.

The invention also proposes to arrange a dispensing tube on the valve or the connector, whereby the dispensing tube commences on the outlet opening and extends the passage to a dispensing tube tip.

In this context, the invention can provide the dispensing tube to comprise a fastening means, in particular an internal thread, through which the dispensing tube is connected to the fastening means of the connector in a detachable manner or through which the dispensing tube is connected to the valve in a fixed manner.

Moreover, the invention can provide the dispensing tube to comprise a static mixer. Moreover, it can be advantageous that the dispensing tube, with the valve being closed, is arranged parallel to the at least one cartridge, in particular between at least two cartridges.

The invention also proposes that the valve, in the open and in the closed position, is arranged in a press-fit manner over the openings on the cartridge heads and closes these in a sealed manner or connects them in a sealed manner to the passage or passages.

Moreover, the invention proposes that the cartridge system comprises at least two cartridges, which are arranged to be parallel to each other, for mixing and applying a mixing ware, in particular a medical cement, preferably three cartridges arranged to be parallel to each other.

In this context, the invention can provide the passages in the valve to connect the openings of at least two cartridges to the outlet opening when the valve is in the open position.

The invention also proposes that the valve is cylinder-shaped, takes the shape of a cylinder with an elliptical base or the shape of a section of a cylinder.

According to the invention, the rotatable cylinder (20, 120, 220, 320, 420, 520) is closed on both narrow sides and preferably tapers conically from one narrow side to the other.

Moreover, the invention proposes the external diameter of the dispensing tube right above the connecting site of the valve, which is provided as a rotatable cylinder, and the dispensing tube preferably to be equal to or smaller than the distance between the yoke-shaped bearings forming the bracket.

The invention can also provide that a bearing has a larger internal diameter than the second bearing, and that the connection site of the rotatable cylinder to the dispensing tube is at a distance to the first bearing that is smaller than half of the external diameter of the dispensing tube right above the connecting site of the rotatable cylinder and the dispensing tube.

The invention also proposes that at least one sealing ring is arranged on the valve that seals the opening or openings in the cartridge or cartridges with the valve in the closed and/or open positions.

In the scope of the invention, the term, flowable material, is understood to mean liquid materials, viscous materials and even highly viscous materials that flow only upon the application of pressure.

BRIEF DESCRIPTION OF THE DRAWINGS

In the following, exemplary embodiments of the invention are illustrated through ten schematic drawings. In the figures.

DETAILED DESCRIPTION

Figure 1:
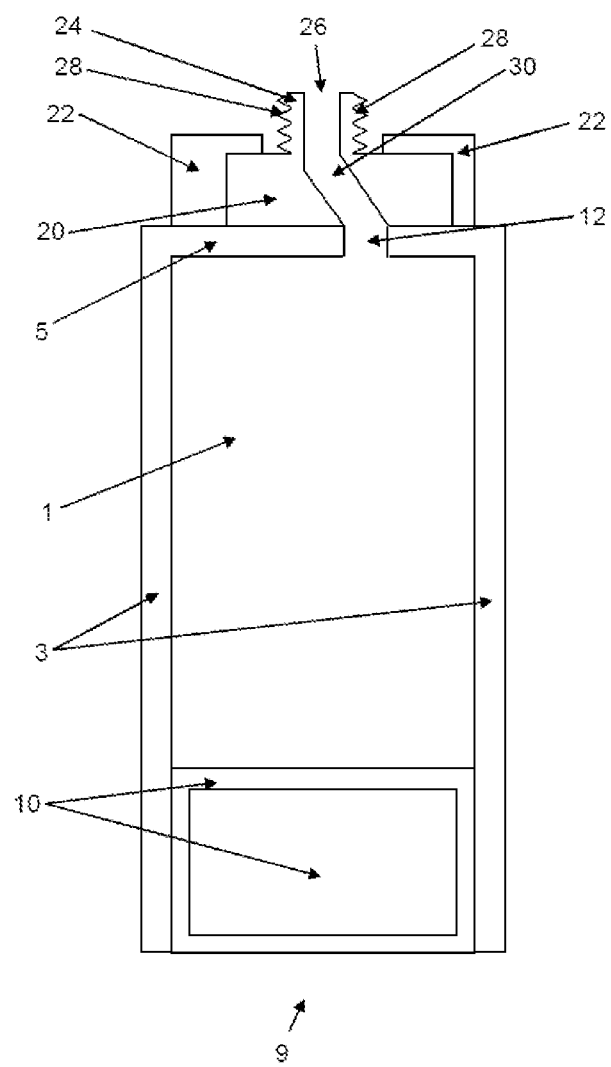
FIG. 1 shows a cross-sectional view in longitudinal direction of a cartridge system according to the invention.

The schematic cross-sectional view shown in FIG. 1 shows a cartridge (1) that is bounded on all sides by cartridge walls (3), on the front side by a cartridge head (5), and from the direction of the cartridge floor (9) by a feed plunger (10). An opening (12) is provided in the wall forming the cartridge head (5), whereby a flowable material (not shown) contained in the cartridge (1) can be expelled through said opening through insertion of the feed plungers (10).

A cylindrical valve (20) is arranged on the cartridge head (5) in a bracket (22) and mounted in the bracket (22) such as to be rotatable about its axis of symmetry. The cartridge head (5) comprises a depression (not shown) shaped like a cylinder jacket section such that the cylindrical valve (20) fits exactly into the depression. The opening (12) is not situated in said depression. The cylindrical valve (20) comprises on one side of its cylinder jacket surface a hollow, cylindrical connector (24) having an outlet opening (26) whose axis of symmetry is arranged to be perpendicular to the axis of symmetry of the valve (20). A thread (28) as fastening means for a dispensing tube (not shown) is arranged on the external surface of the connector (24).

On the inside of the otherwise solid cylindrical valve (20), a passage (30) is arranged that extends the opening of the connector (24) opposite from the outlet opening (26) through the cylindrical valve (20) to the side of the valve (20) that is opposite to the connector (24). The two openings that are provided in the valve (20) are arranged at an offset with respect to each other. What this achieves is that a depression (not shown) for the connector (24) can be provided in the cartridge head (5), into which the connector (24) can be sunk upon a rotation of the valve (20) without affecting the opening (12) in cartridge head (5). However, the two openings in the valve (20) can just as well be arranged directly opposite from each other, i.e. not at an offset with respect to each other.

There is a continuous opening from the cartridge (1) via the opening (12) and the passage (30) to the outlet opening (26) such that the flowable material can be expelled from the inside of the cartridges (1) through the continuous opening out of the cartridge system. The closure of the cartridge system, which is formed by the valve (20) that is mounted such as to be rotatable about its axis of symmetry, is also open.

Rotating the valve (20) and its axis of symmetry by, for example, 90°, the opening (12) is closed through the cylinder jacket wall of the cylindrical valve (20). The closure of the cartridge system then is situated in the closed state and a flowable material cannot exit from the inside of the cartridge (1).

The bracket (22) can consist of two bearings that do not need to be identical in structure. The bearings being asymmetrical in shape is advantageous in that the valve (20) can be installed in the bracket (22) in one certain orientation only.

Alternatively, the valve (20) can just as well extend through the bracket (22), whereby the connector (24) is arranged outside, rather than between, the two bearings of the bracket (22) on the valve (20). Rotating the valve (20) by 180° about its axis of symmetry, the connector (24) is situated laterally next to the cartridge (1) provided the distance from the bracket (22) is sufficient. The invention can also provide a dispensing tube (not shown), which is connected to the connector (24) to be arranged next to the cartridge (1) in said closed position of the valve (20) which provides for a compact design of the cartridge system.

Figure 2:
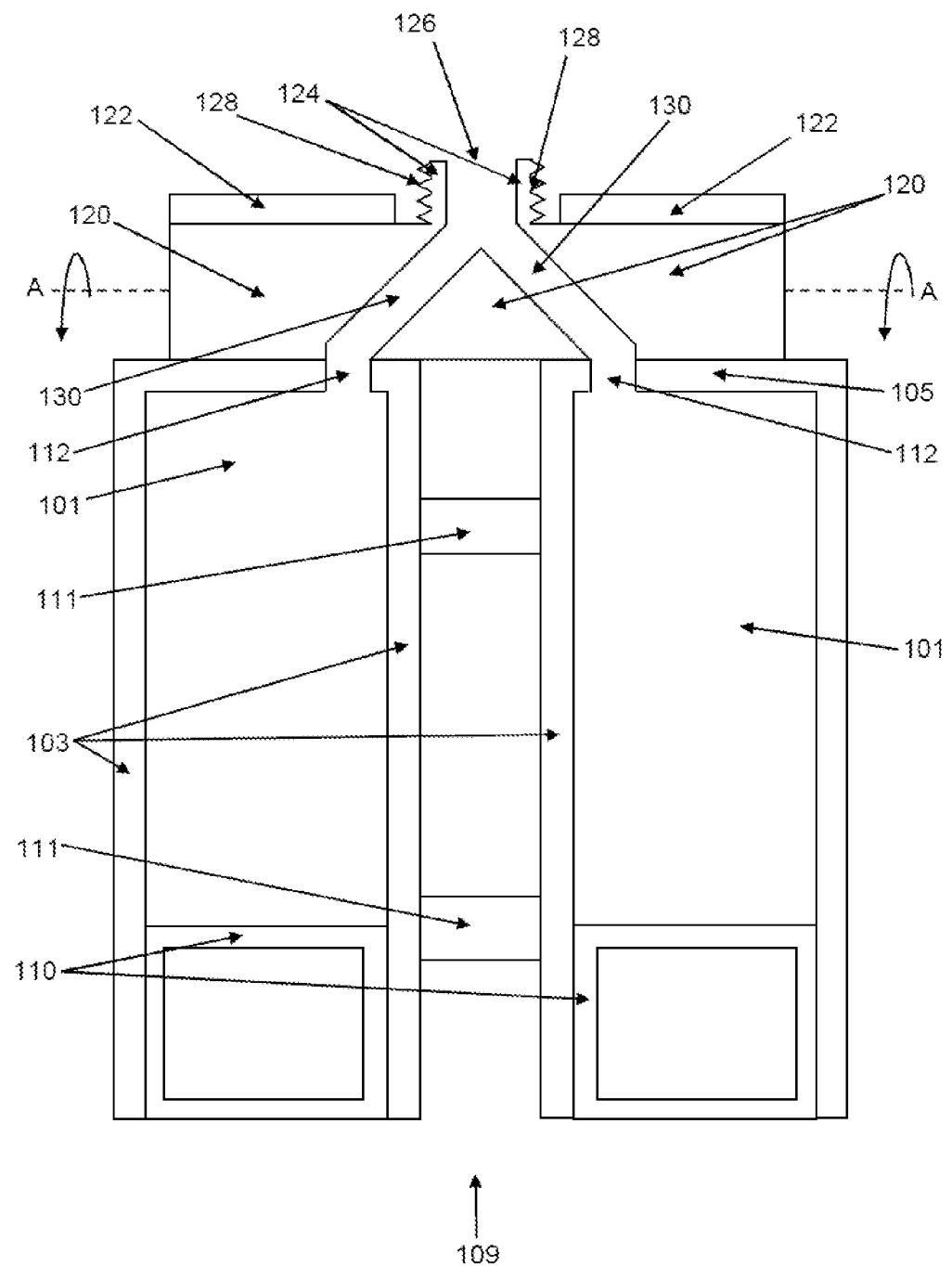
FIG. 2 shows a cross-sectional view in longitudinal direction of a second cartridge system according to the invention with open closure.

FIG. 2 shows a schematic cross-sectional view of a second cartridge system according to the invention that is suitable for mixing a mixing ware consisting of two or more components. For this purpose, the cartridge system comprises at least two cartridges (101) that contain the starting components of the mixing ware, which consist of flowable materials. Aside from the two cartridges (101) shown in FIG. 2, more cartridges can be provided just as well and are arranged, for example, behind the two cartridges (101) shown. The cartridges (101) are bounded by cartridge walls (103) on the side and by cartridge heads (105) on the front side. From the direction of the cartridge floor (109), the cartridges (101) are closed in a gas-tight manner through feed plungers (110) such that the cartridge content can be squeezed from the cartridges (101) by applying compressed air to the feed plungers (110). The two cartridges (101) are connected to each other in a fixed manner through fins (111). Openings (112) are provided in the cartridge heads (105).

Above the two openings (112), a valve (120) is arranged on the cartridge heads (105) and is mounted, such as to be rotatable about rotation axis (A), in a bracket (122), which is connected to the cartridge heads (105) in a fixed manner. A cylindrical connector (124) that is provided as a hollow body and comprises an outlet opening (126) and an external thread (128) is arranged on one side of the valve (120). The bracket (122) includes a cut-out in this region. For this purpose, the bracket (122) can be made up by two parts. The external thread (128) is suitable for fastening a dispensing tube (not shown) having a matching internal thread.

On the inside of the valve (120) are situated two passages (130), which, in the open position of the valve (120) shown in FIG. 2, form a continuous connection from the two openings (112) of the cartridges (101) to the outlet opening (126). Applying pressure to the feed plungers (110), the flowable material (not shown) contained in the cartridges (101) is squeezed from the cartridges through the openings (112) and the passages (130) into the connector (124), in which the two starting components are mixed to form a mixing ware. The mixing ware can be applied either directly through the outlet opening (126) or a dispensing tube (not shown) is attached on the outlet opening (126) and contains a static mixer such that the two starting components are mixed more thoroughly in the dispensing tube. The mixing ware can then be applied through a dispensing tube tip of the dispensing tube.

Figure 3:
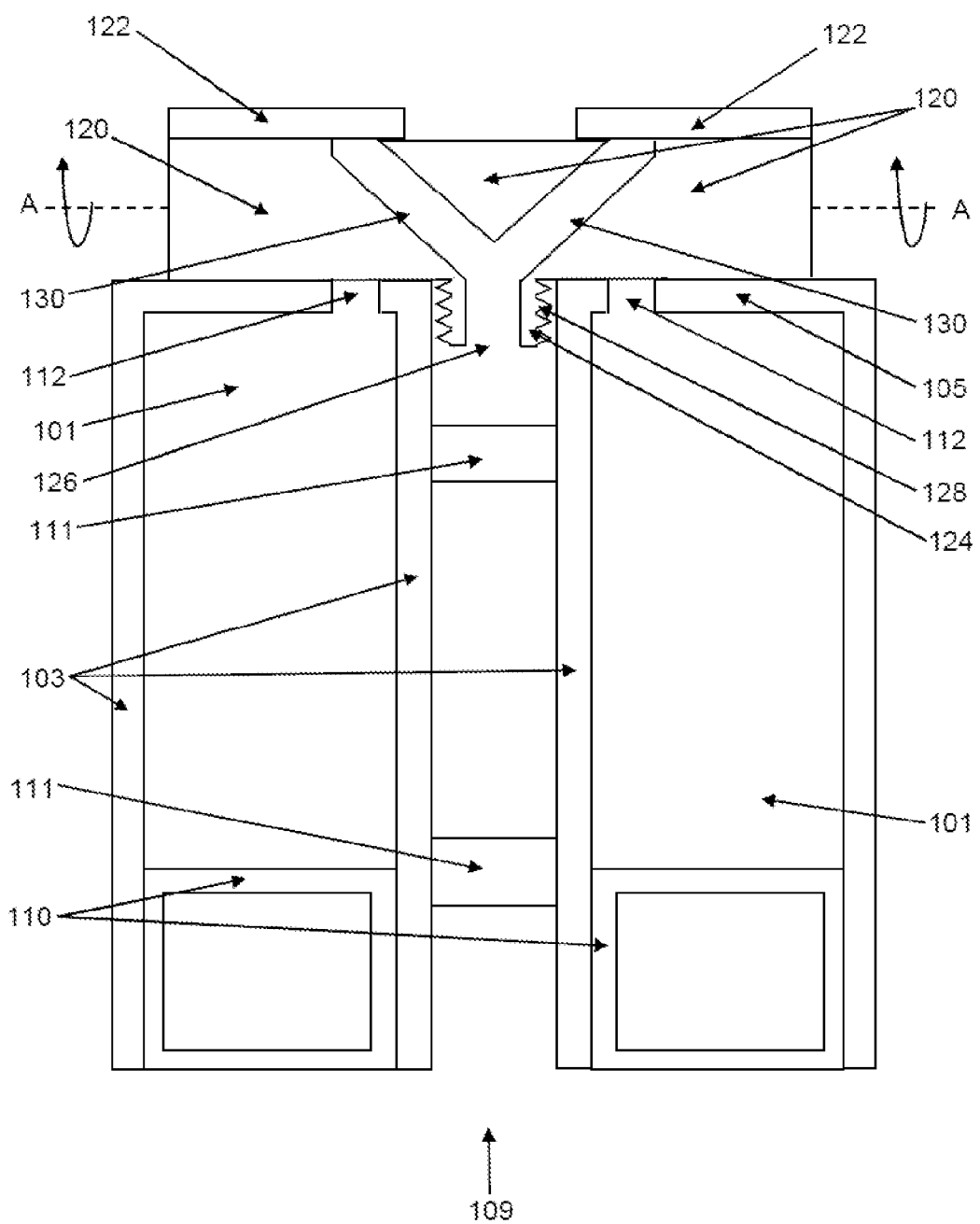
FIG. 3 shows a cross-sectional view in longitudinal direction of the second cartridge system according to the invention according to FIG. 2 with closed closure.

The openings (112), and therefore the cartridge system, can be closed by rotating the valve (120) about the rotation axis (A). An arrangement of this type is shown as a schematic cross-sectional view in FIG. 3. Rotating the valve (120) by 180° closes the two openings (112) of the cartridges (101). The connector (124) having the outlet opening (126) and the thread (128) is positioned in the intervening space between the two cartridges (101) that is bounded through the cartridge walls (103) facing it. For this purpose, the distance between the two cartridges (101) is sufficiently large to take up the entire width of the connector (124). The valve (120) sits in a press-fit manner on the regions of the cartridge heads (105) that surround the openings (112). For this purpose, an external shape of the valve seat on the cartridge heads (105) is adapted to an external shape of the valve (120). If a dispensing tube (not shown) is to be installed on the connector (124), in particular installed in a fixed manner, the distance between the two cartridges (101) may need to be selected even larger.

Figure 4:
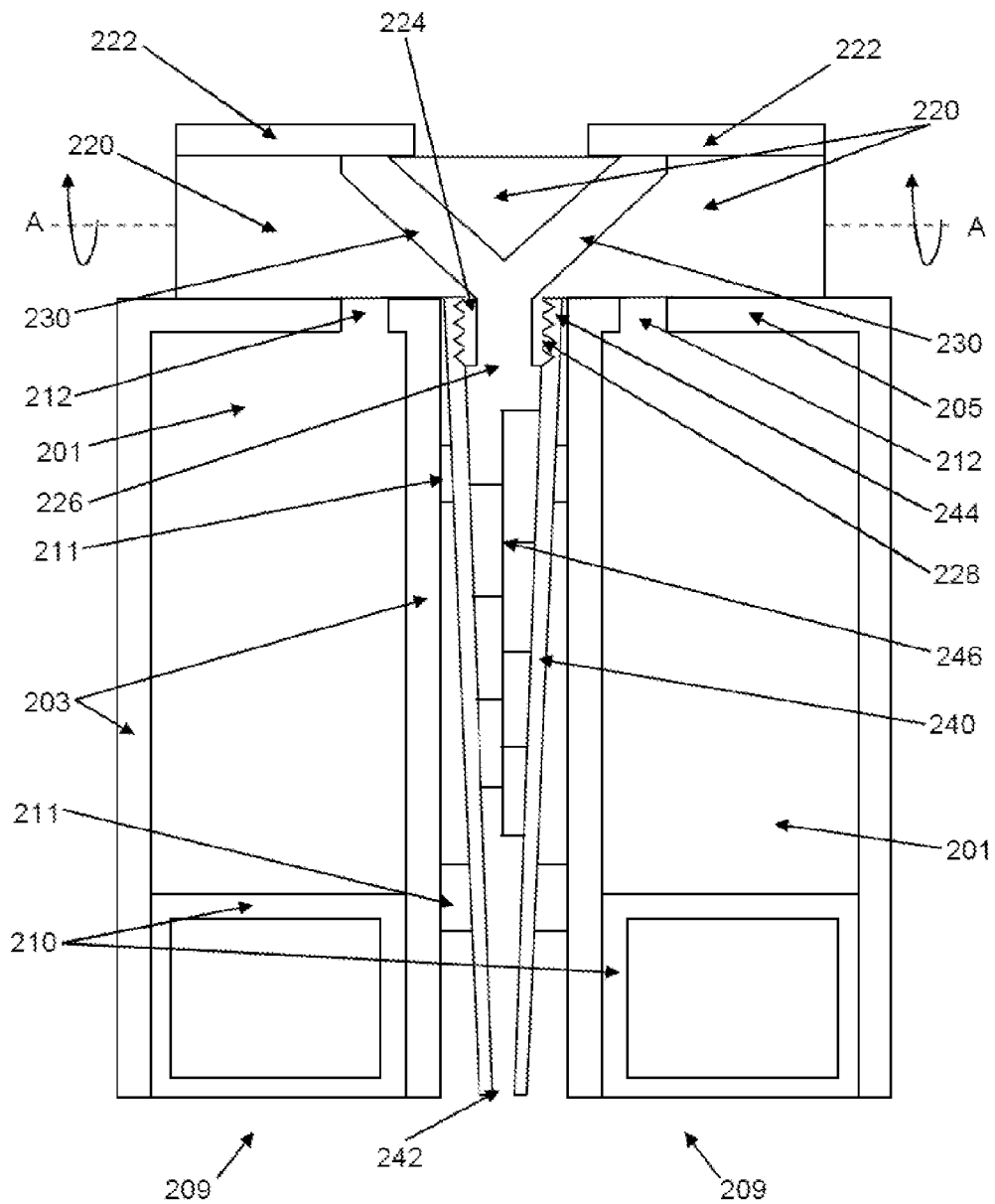
FIG. 4 shows a cross-sectional view in longitudinal direction of a third cartridge system according to the invention with closed closure and dispensing tube.

Said constellation is shown as a schematic drawing for a third exemplary embodiment in FIG. 4. There is sufficient space for the full width of a dispensing tube (240) between two cartridges (201) that are connected to each other through fins (211). The cartridges (201) are closed on the sides, top side, and bottom side through cartridge walls (203), through cartridge heads (205), and through feed plungers (210), respectively. The feed plungers (210) can be inserted into the cartridges (201) proceeding from the direction of the cartridge floors (209). Openings (212) for flowable materials that are stored in the cartridges (201) are situated in the cartridge heads (205).

A valve (220) in the form of a cylinder is mounted in a bracket (222) such as to be rotatable about the axis of symmetry (A) of the cylinder as rotation axis (A). A connector (224) having a thread (228) is situated on a cylinder jacket surface of the valve (220). The connector (224) is open in upward direction and there forms an outlet opening (226). Passages (230) are arranged in the valve (220) that connect two openings on the side opposite from the connector (224) to the outlet opening (226). The two openings (212) are closed by means of the cylinder wall jackets of the valve (220). Rotating the closed valve (220) by 180° about rotational axis (A), the two openings in the valve (220) become situated over the openings (212) of the cartridges (201). The cartridge system, i.e. the closure, i.e. the valve (220), is closed in this state.

The dispensing tube (240) is hollow on the inside and terminates into a dispensing tube tip (242). On the opposite side, the dispensing tube (240) comprises a fastening means (244) in the form of an internal thread. The internal thread (244) of the dispensing tube (240) is screwed onto the external thread (228) of the connector (224). Alternatively, the dispensing tube (240) can just as well be connected in a fixed manner to the connector (224). A static mixer (246) is arranged inside the dispensing tube (240).

The fins (211) must have a curvature (towards the back in the plane of the drawing) such that the dispensing tube (240) can be positioned exactly between the two cartridges (201). Moreover, the two fins (211) must not impede the tilting motion of the dispensing tube (240) caused by a rotation of the valve (220). Rotating the valve (220) about the rotation axis (A) transitions the closure of the cartridge system from the closed to the open state. The dispensing tube (240) is swiveled by 180° simultaneously.

Figure 5:
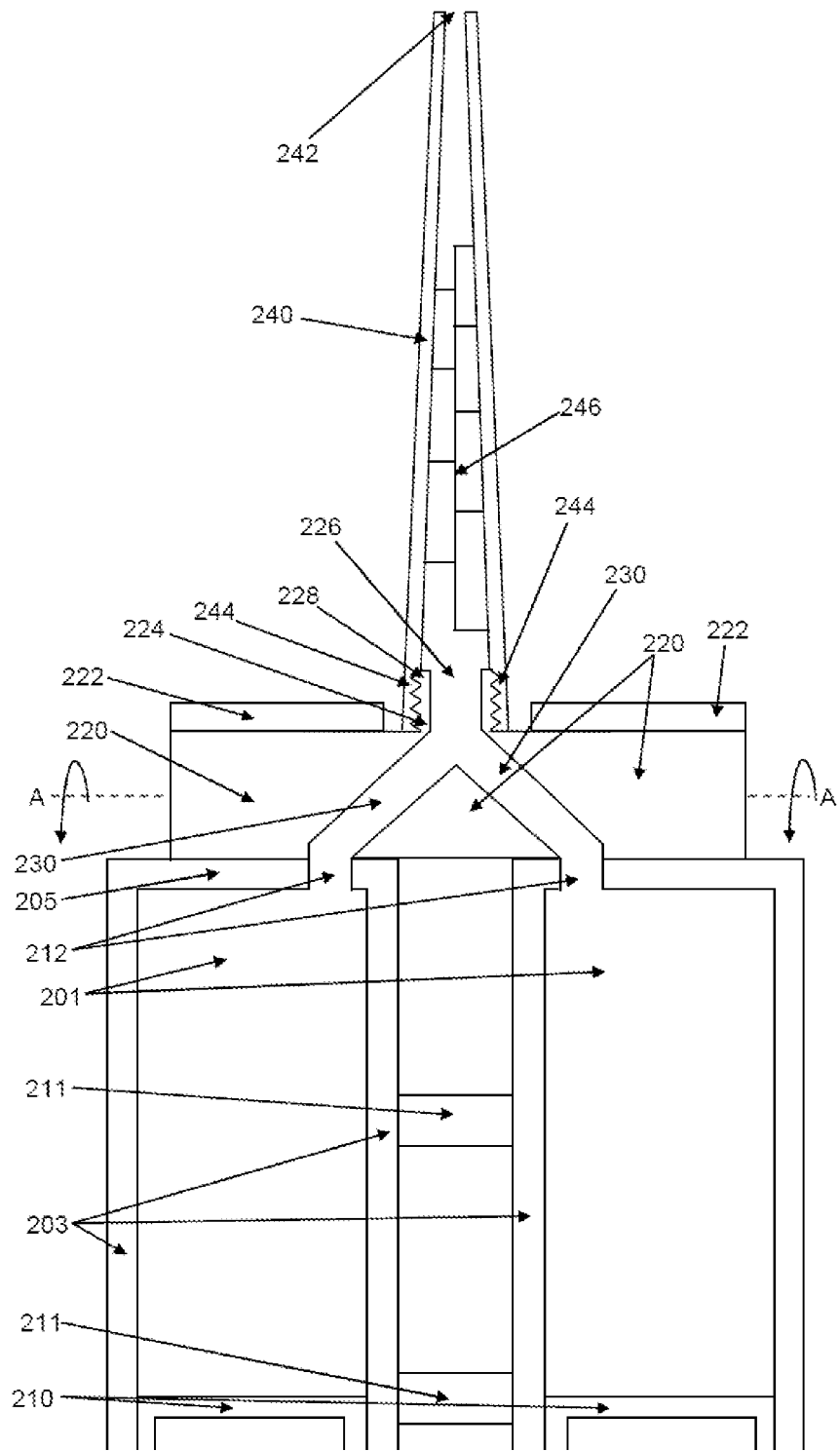
FIG. 5 shows a cross-sectional view in longitudinal direction of the third cartridge system according to the invention according to FIG. 4 with open closure and dispensing tube.

Said open state of the cartridge system is shown as a schematic longitudinal section in FIG. 5. The two openings of the valve (220) opposite from the connector (224) are situated over the openings (212) of the cartridges (201) in the open state of the valve (220). By this means, a connection is established between the openings (212) and the inside of the dispensing tube (240) through the passages (230).

Accordingly, if an external force is applied onto the feed plungers (210), for example through compressed air, the content of the cartridges (201) is fed through the openings (212) via the passages (230) and the outlet opening (226) into the dispensing tube (240). Therein, the static mixer (246) is used to mix the contents of the cartridges (201) and the resulting mixing ware is squeezed out of the dispensing tube tip (242).

Figure 6:
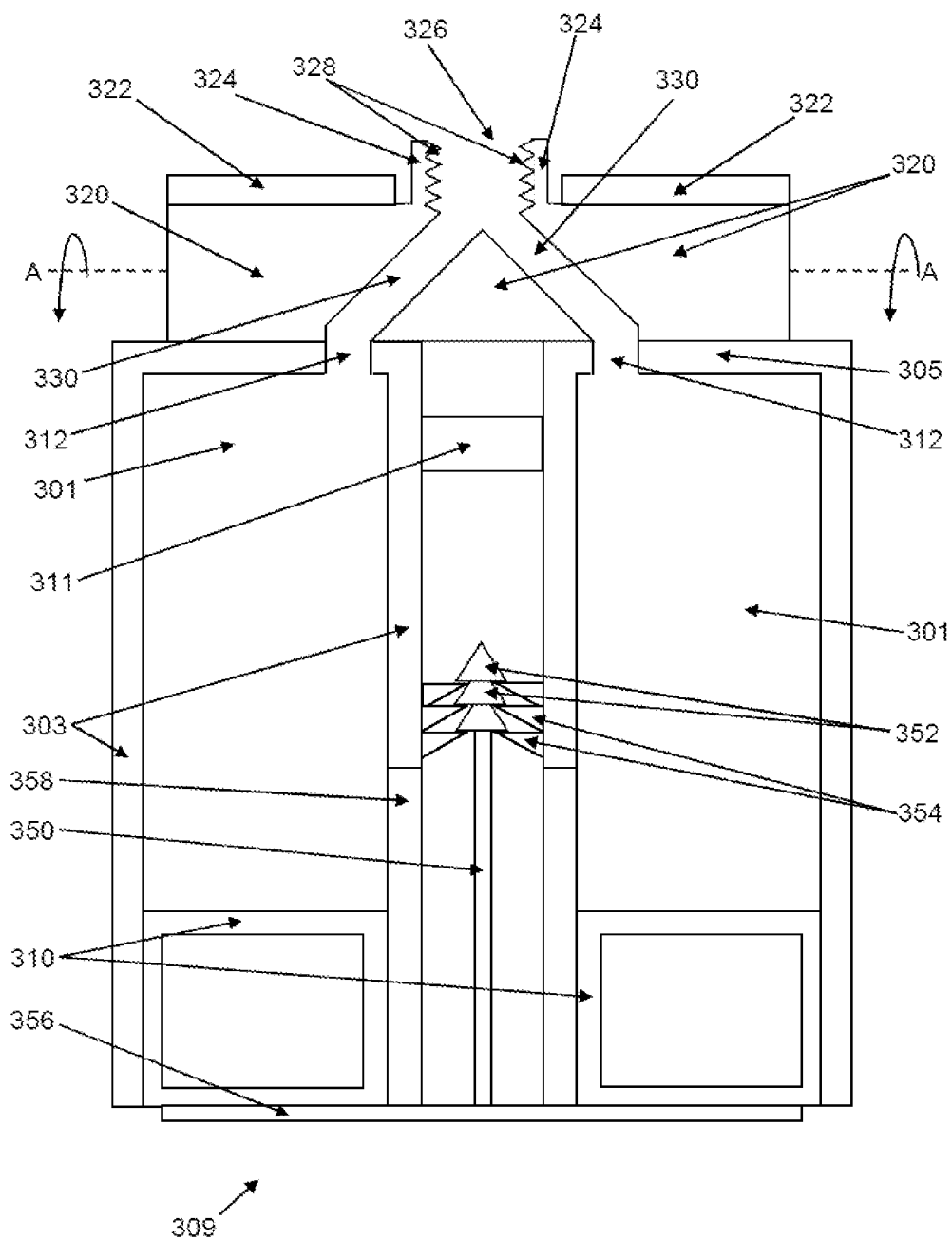
FIG. 6 shows a cross-sectional view in longitudinal direction of a fourth cartridge system according to the invention with open closure and locking device.

FIG. 6 shows a schematic cross-sectional view of a fourth exemplary embodiment according to the invention. Two cartridges (301) that are bounded by cartridge walls (303), a cartridge head (305) on the front side, and feed plungers (310) on the side of the cartridge floor (309), each have an opening (312) in the cartridge head (305). The two cartridges (301) are connected to each other through a fin (311). A cylindrical valve (320) is mounted in a bracket (322) on the cartridge heads (305) such as to be rotatable about the rotation axis (A). Passages (330) inside the valve (320) connect the openings (312) to an outlet opening (326) that is arranged on the opposite side of the valve (320). A connector (324) is arranged on the valve (320) in the region of the outlet opening (326). The connector (324) is a hollow body and has fastening means (328) in the form of an internal thread or a snap-in locking means arranged on its inside.

A rod (350) is arranged between the two cartridges (301) and has a snap-in locking means (352) provided on its tip. The snap-in locking means (352) can engage an opposite snap-in locking means (354) that is arranged on the external cartridge walls (303) of the cartridges (301) facing the intervening space. As soon as the snap-in locking means (352) engage the opposite snap-in locking means (354), any motion of the rod (350) in the direction of the cartridge floor (309) is prevented. A fin (356) connecting the two feed plungers (310) and the rod (350) to each other in a fixed manner is arranged on the cartridge floor (309). The intervening space can just as well be structured as a partly-closed hollow body about which the cartridges (301) are arranged.

Due to the fin (356), the feed plungers (310) and the rod (350) can only move synchronously. The fin (356) can be moved through the cartridge walls (303) by means of a slit (358) in order to allow feed plungers (310) to be pushed far into the inside of the cartridges (301). Alternatively, the fin (356) could just as well be designed as a double-arch, or be connected through rods to the feed plungers (310) and the rod (350), without any need to have slits (358) in the cartridge walls (303).

Figures 7A, 7B:
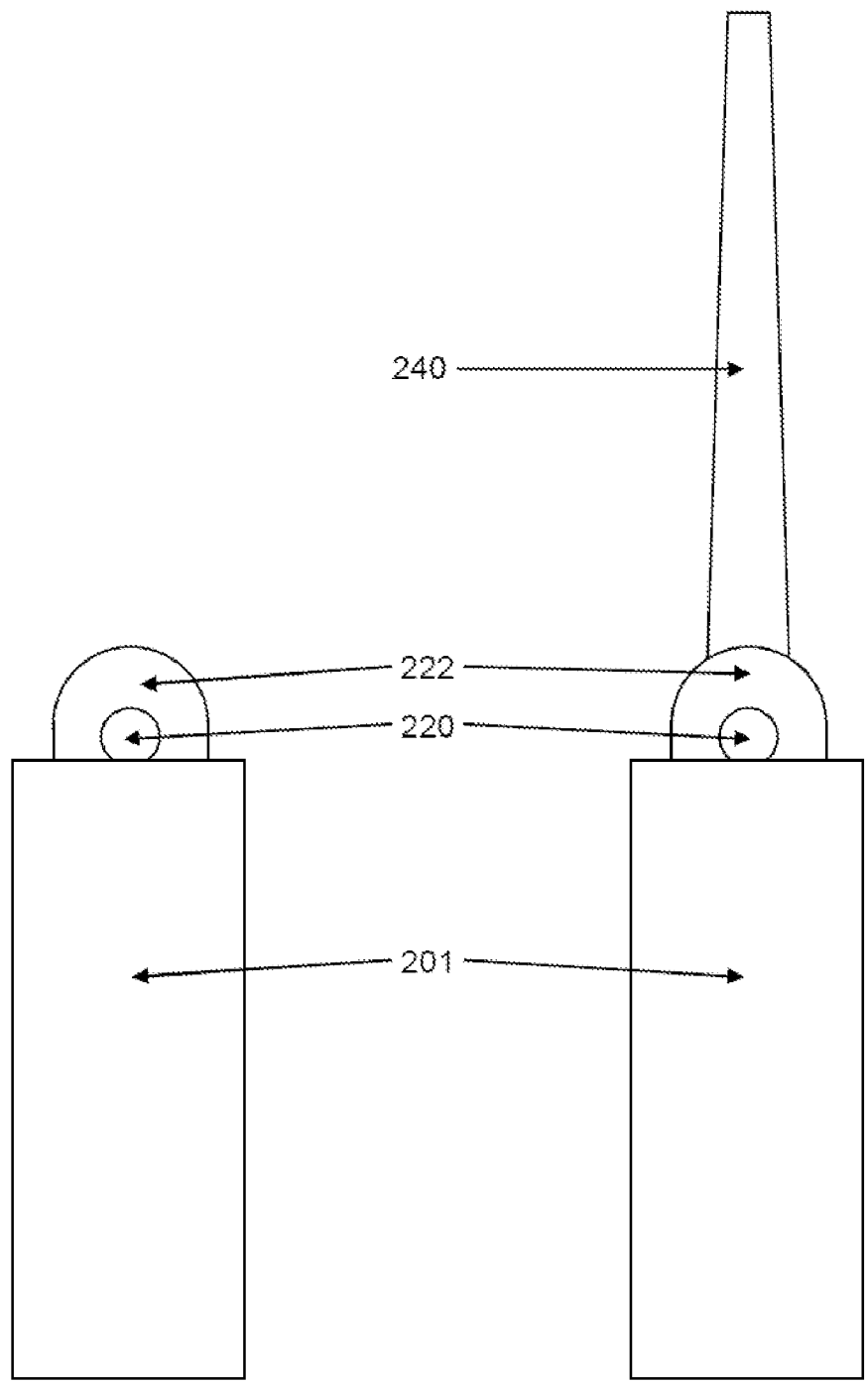
FIG. 7a) shows a side view of the third cartridge system according to the invention according to FIG. 4 with closed closure and dispensing tube.
FIG. 7b) shows a side view of the third cartridge system according to the invention according to FIG. 5 with open closure and dispensing tube.

FIG. 7a) shows a closed cartridge system with dispensing tube folded-in according to FIG. 4 as a top view onto the side of the cartridge system. The rotatable valve (220) is arranged in the bracket (222) above the cartridge (201). The dispensing tube is not shown here since it is situated between the cartridges (201).

FIG. 7b) shows an open cartridge system with dispensing tube (240) folded-out according to FIG. 5 as a top view onto the side of the cartridge system. The dispensing tube (240) can be seen above the bracket (222) for the rotatable valve (220). The rotatable valve (220) is connected in a fixed manner to the cartridge (201) through the bracket (222).

Figure 8:
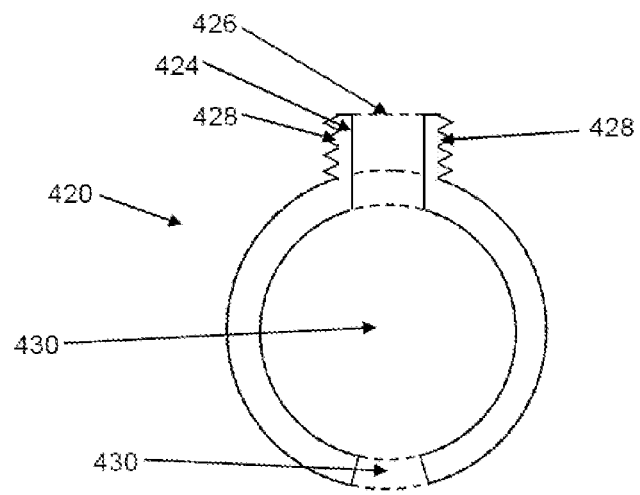
FIG. 8 shows a cross-sectional view in transverse direction of a closure according to the invention.

FIG. 8 shows a schematic cross-sectional view of a valve (420), which is to be mounted in a rotatable manner, for a closure according to the invention for a cartridge system according to the invention. The valve (420) comprises on its top side a hollow connector (424) having an external thread (428). The connector (424) terminates in an outlet opening (426). An opening is provided on the underside of the valve (420). The entire valve (420) is hollow on the inside. The hollow space on the inside of the valve (420) and the lower opening jointly form a passage (430) through the valve (420).

Figure 9:
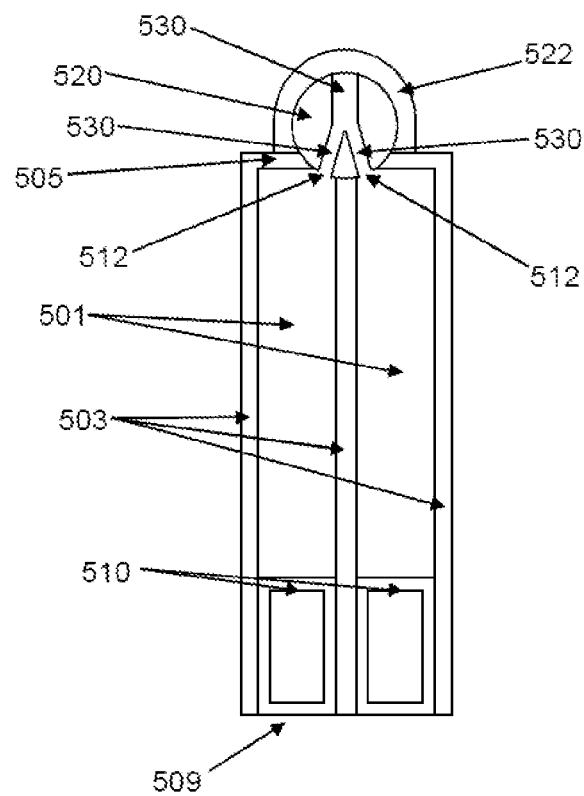
FIG. 9 shows a cross-sectional view in longitudinal direction of a fourth cartridge system according to the invention with open closure.

FIG. 9 shows a cross-sectional view of a fifth exemplary embodiment of a cartridge system according to the invention. Two cartridges (501) that are closed on the side, on top, and on the bottom through cartridge walls (503), cartridge heads (505), and gas-tight feed plungers (510), respectively, comprise openings (512) in the cartridge heads (505). A cylindrical valve (520) is situated in press-fit manner with respect to the cartridge heads (505) and is mounted in a rotatable manner in a bracket (522) on the cartridge heads (505). Passages (530) are situated on the inside of the valve (520) and, In the open position of the valve (520), form a passage from the openings (512) to an outlet opening (not shown) that is arranged in the valve (520) such as to be opposite from the cartridge heads (505). Applying pressure onto the feed plungers (510) from the direction of the cartridge floor (509), the content of the cartridges (501) can be squeezed from the cartridge system through the valve (520).

Rotation of the valve (520) allows the openings (512) and thus the cartridge system to be closed completely. According to the design of the fifth exemplary embodiment, the valve (520) is oriented rotated perpendicular to its axis of symmetry as compared to the other exemplary embodiments. A further cartridge having a further opening (not shown) is arranged behind the two cartridges (501). A further passage (not shown) extends from said further opening through the valve (520) to the outlet opening. By this means, three cartridges are connected to the outlet opening such that a mixing ware can be produced from three components using a cartridge system of this type.

The exemplary embodiments can easily be generalised to a cartridge system comprising three, four, five or more cartridges. If the starting components need to be mixed at a mixing ratio other than in equal fractions in order to obtain the desired mixing ware, the ratio of the cross-sectional areas of the cartridges (1, 101, 201, 301, 501) can be adjusted to the mixing ratio. Advancement of the feed plungers (10, 110, 210, 310, 510) at the same speed then results in a mixture having the desired mixing ratio. Advancement at equal speed can be ensured by connecting all feed plungers (10, 110, 210, 310, 510) to one or more fins (111, 211, 311) in a fixed manner. Alternatively, a certain mixing ratio can also be established through having a transmission or a suitable gearing advance the various feed plungers (10, 110, 210, 310, 510) at different speeds. Variation of the advancement speed of the various feed plungers (10, 110, 210, 310, 510) allows the mixing ratio of the starting components to be varied while they are being expelled and thus allows different physical properties of the squeezed-out mixing ware to be attained. By this means, gradients of properties are generated in the mixing ware that is produced. Using a cement or adhesive as an example, compound materials can thus be made that have improved stability as compared to homogeneous compounds.

Accordingly, a cartridge system according to the invention can be characterised a) in that a dispensing tube (240) is arranged;
b) in that the dispensing tube (240) is connected on one end to a rotatable cylinder (20, 120, 220, 320, 420, 520);
c) in that the rotatable cylinder (20, 120, 220, 320, 420, 520) includes at least two openings that are connected to each other;
d) whereby at least one opening in the cylinder (20, 120, 220, 320, 420, 520) is connected in a continuous manner to the dispensing tube (240);
e) in that the rotatable cylinder (20, 120, 220, 320, 420, 520) is mounted in a bracket (22, 122, 222, 322, 522) comprising at least two yoke-shaped bearings (22, 122, 222, 322, 522) that are connected to a cartridge head (5, 105, 205, 305, 505) or more cartridge heads (5, 105, 205, 305, 505);
f) in that at least one opening (12, 112, 212, 312, 512) is present in the cartridge head (5, 105, 205, 305, 505) or cartridge heads (5, 105, 205, 305, 505) and is connected in continuous manner to the inside space of the cartridge (1, 101, 201, 301, 501) or the inside spaces of the cartridges (1, 101, 201, 301, 501);
g) in that the dispensing tube (240) connected to the rotatable cylinder (20, 120, 220, 320, 420, 520) is arranged between the yoke-shaped bearings (22, 122, 222, 322, 522);
h) in that the cylinder (20, 120, 220, 320, 420, 520) is arranged such as to be rotatable about its cylinder axis by at least 80°; and
i) in that the rotatable cylinder (20, 120, 220, 320, 420, 520) and the opening or openings of the cylinder (20, 120, 220, 320, 420, 520) and the opening or openings (12, 112, 212, 312, 512) of the cartridge (1, 101, 201, 301, 501) or cartridges (1, 101, 201, 301, 501) and the yoke-shaped bearings (22, 122, 222, 322, 522) together form at least one valve (20, 120, 220, 320, 420, 520).

According to the invention, the rotatable cylinder (20, 120, 220, 320, 420, 520) is closed on both narrow sides and preferably tapers conically from one narrow side to the other.

Moreover, the invention proposes the external diameter of the dispensing tube (240) right above the connecting site of the rotatable cylinder (20, 120, 220, 320, 420, 520) and the dispensing tube (240) preferably to be equal to or smaller than the distance between the yoke-shaped bearings (22, 122, 222, 322, 522).

The invention can also provide that a bearing (22, 122, 222, 322, 522) has a larger internal diameter than the second bearing (22, 122, 222, 322, 522) and that the connecting site of the rotatable cylinder (20, 120, 220, 320, 420, 520) to the dispensing tube (240) is at a distance to the first bearing (22, 122, 222, 322, 522) that is smaller than half the external diameter of the dispensing tube (240) right above the connecting site of the rotatable cylinder (20, 120, 220, 320, 420, 520) to the dispensing tube (240).

The dispensing tube (240) is connected to the cartridge (1, 101, 201, 301, 501) or cartridges (1, 101, 201, 301, 501) through the rotatable cylinder (20, 120, 220, 320, 420, 520) that is situated in at least two yoke-shaped bearings (22, 122, 222, 322, 522) of the bracket (22, 122, 222, 322, 522). The cartridge closure system according to the invention works such that the dispensing tube (240) is rotated in the direction of the cartridge floor (9, 109, 209, 309, 509) in the closed state. The dispensing tube (240) preferably is positioned parallel to the cartridge (1, 101, 201, 301, 501) or cartridges (1, 101, 201, 301, 501). For the opening process, the dispensing tube (240), which is folded downwards in the direction of the cartridge floor (9, 109, 209, 309, 509), is simply rotated upwards in the direction of the cartridge head (5, 105, 205, 305, 505) or cartridge heads (5, 105, 205, 305, 505). When the dispensing tube (240) is rotated downwards in the direction of the cartridge floor (9, 109, 209, 309, 509), the opening or openings in the cylinder (20, 120, 220, 320, 420, 520) are not situated to coincide with the opening (12, 112, 212, 312, 512) or openings (12, 112, 212, 312, 512) of the cartridge head (5, 105, 205, 305, 505) or cartridge heads (5, 105, 205, 305, 505). Rotating the dispensing tube (240) upwards rotates the rotatable cylinder (20, 120, 220, 320, 420, 520) in a manner such that the opening or openings in the cylinder (20, 120, 220, 320, 420, 520) is or are situated to coincide with the opening (12, 112, 212, 312, 512) or openings (12, 112, 212, 312, 512) in the cartridge head (5, 105, 205, 305, 505).

This means that the user simply needs to fold the dispensing tube (240) upwards in the direction of the cartridge head (5, 105, 205, 305, 505) into the application position to open the valve (20, 120, 220, 320, 420, 520) and thus the cartridge (1, 101, 201, 301, 501) or cartridges (1, 101, 201, 301, 501). The user does not need to connect the dispensing tube (240) to the cartridge (1, 101, 201, 301, 501) or cartridges (1, 101, 201, 301, 501). This excludes any mounting error during the application by design. With respect to the use of multi-component cartridges, all cartridges (1, 101, 201, 301, 501) are opened synchronously through the rotation of the dispensing tube (240) and thus of the rotatable cylinder (20, 120, 220, 320, 420, 520). It is also advantageous that the dispensing tube (240) is connected to the cartridge (1, 101, 201, 301, 501) or cartridges (1, 101, 201, 301, 501). The dispensing tube (240) can thus not be lost before the application while unpacking the packaging means. Moreover, no separate packaging means are needed for the dispensing tube (240).

The cartridge closure system according to the invention provides the user with a system that can be operated rapidly, easily, and safely.

As an advantageous development of the invention, snap-in locking devices that are common in the plastics industry, for example in the form of pegs that are mobile in one direction, can be arranged on the bearings (22, 122, 222, 322, 522) and fix the dispensing tube (240) in the application position and prevent the dispensing tube (240) from rotating in reverse direction from the application position. Another advantageous development has snap-in locking devices that are common in the plastics industry attached on the underside of the rotatable cylinder (20, 120, 220, 320, 420, 520) and prevent the dispensing tube (240) from rotating in reverse direction from the application position.

According to the invention, the rotatable cylinder (20, 120, 220, 320, 420, 520) is closed on both narrow sides and preferably tapers conically from one narrow side to the other. By this means, the rotatable cylinder (20, 120, 220, 320, 420, 520) can be mounted in the bearings (22, 122, 222, 322, 522) without any difficulty.

The invention can also provide the cylinder (20, 120, 220, 320, 420, 520) to be situated in a press-fit in the yoke-shaped bearings (22, 122, 222, 322, 522). A sufficient sealing effect is attained through the press-fit. Furthermore, according to the invention, additional sealing rings can be arranged on the rotatable cylinder (20, 120, 220, 320, 420, 520) provided this is necessitated by the properties of the flowable materials to be stored in the cartridges (1, 101, 201, 301, 501). If just one of the starting components for a mixing ware is sufficiently inviscid for the connection to be insufficiently sealed in the absence of a sealing ring, it is sufficient that the respective opening (12, 112, 212, 312, 512) on the valve (20, 120, 220, 320, 420, 520) has, in addition, a sealing ring for the closed and the open position assigned to it.

Moreover, the invention provides the external diameter of the dispensing tube (240) right above the connecting site of the rotatable cylinder (20, 120, 220, 320, 420, 520) and the dispensing tube (240) preferably to be equal to or smaller than the distance between the yoke-shaped bearings (22, 122, 222, 322, 522). The dispensing tube (240) fixes the cylinder (20, 120, 220, 320, 420, 520) in place between the bearings (22, 122, 222, 322, 522). By this means, the cylinder (20, 120, 220, 320, 420, 520) cannot slip out.

It is advantageous that a first bearing (22, 122, 222, 322, 522) has a larger internal diameter than the second bearing (22, 122, 222, 322, 522) and that the middle of the connecting site of the rotatable cylinder (20, 120, 220, 320, 420, 520) to the dispensing tube (240) is at a distance to the first bearing (22, 122, 222, 322, 522) that is smaller than half the external diameter of the dispensing tube (240) right above the connecting site of the rotatable cylinder (20, 120, 220, 320, 420, 520) to the dispensing tube (240). This renders the rotatable cylinder (20, 120, 220, 320, 420, 520) easier to install. If half the external diameter of the dispensing tube (240) is slightly larger than the distance of the middle of the connecting site of the rotatable cylinder (20) to the dispensing tube (240), the dispensing tube (240) presses the rotatable cylinder (20, 120, 220, 320, 420, 520) into the bearings (22, 122, 222, 322, 522). This not only prevents the rotatable cylinder from slipping out, but the cylinder (20, 120, 220, 320, 420, 520) is also strongly pressed into the bracket (22, 122, 222, 322, 522).

The invention can provide the openings of the rotatable cylinder (20, 120, 220, 320, 420, 520) and the openings (12, 112, 212, 312, 512) of the cartridge head (5, 105, 205, 305, 505) or cartridge heads (5, 105, 205, 305, 505) to form at least one connection between the internal space of the cartridge (1, 101, 201, 301, 501) or the internal spaces of the cartridges (1, 101, 201, 301, 501) that is permeable for flowable materials, when the axis of the dispensing tube (240) is situated to be parallel to the longitudinal axis of the cartridge (1, 101, 201, 301, 501) or the longitudinal axes of the cartridges (1, 101, 201, 301, 501) and the outlet of the dispensing tube tip (242) of the dispensing tube (240) is situated in the direction opposite to the cartridge head (5, 105, 205, 305, 505) or cartridge heads (5, 105, 205, 305, 505).

Moreover, the invention can provide the openings of the rotatable cylinder (20, 120, 220, 320, 420, 520) and the openings (12, 112, 212, 312, 512) of the cartridge head (5, 105, 205, 305, 505) or cartridge heads (5, 105, 205, 305, 505) to form at least one connection between the internal space of the cartridge (1, 101, 201, 301, 501) or the internal spaces of the cartridges (1, 101, 201, 301, 501) that is not permeable for pasty materials, when the dispensing tube (240) is situated next to the cartridge (1, 101, 201, 301, 501) or between the cartridges (1, 101, 201, 301, 501) and the dispensing tube tip (242) of the dispensing tube (240) is situated in the direction facing the cartridge floor (9, 109, 209, 309, 509) or cartridge floors (9, 109, 209, 309, 509).

A cartridge system for multiple components having the cartridge closure system according to the invention can provide a) two or more cartridges (101, 201, 301, 501) to be arranged about an internal hollow cylinder or an internal irregularly- or regularly-shaped hollow body and have longitudinal axes that are parallel to the axis of the internal hollow cylinder or irregularly- or regularly-shaped hollow body;

b) one or more openings (112, 212, 312, 512) to be arranged in the cartridge heads (105, 205, 305, 505);

c) a dispensing tube (240) to be arranged;

d) the dispensing tube (240) to be connected on one end to a rotatable cylinder (120, 220, 320, 420, 520);

e) the rotatable cylinder (120, 220, 320, 420, 520) to possess at least two openings that are connected to each other, whereby at least one opening is connected in a continuous manner to the dispensing tube (240);

f) the rotatable cylinder (120, 220, 320, 420, 520) to be mounted in at least two yoke-shaped bearings (122, 222, 322, 522) that are connected to at least one cartridge head (105, 205, 305, 505);

g) at least one opening (112, 212, 312, 512) to be present in the cartridge heads (105, 205, 305, 505) and to be connected in a continuous manner to the inside space of at least one of the cartridges (101, 201, 301, 501);

h) the dispensing tube (240) that is connected to the rotatable cylinder (120, 220, 320, 420, 520) to be arranged between the yoke-shaped bearings (122, 222, 322, 522);

i) the cylinder (120, 220, 320, 420, 520) to be arranged such as to be rotatable about its cylinder axis (A) by at least 80°;

j) the cartridges (101, 201, 301, 501) to be closed through feed plungers (110, 210, 310, 510);
k) the feed plungers (110, 210, 310, 510) to be connected to each other through a fin (111, 211, 311) or more fins (111, 211, 311) on the side that faces away from the cartridge floor (109, 209, 309, 509);
l) a rod (350) to be arranged in longitudinal direction of the feed plungers (110, 210, 310, 510) in the internal hollow cylinder or the internal irregularly- or regularly-shaped hollow body, and to be connected by one of its ends on at least one fin (111, 211, 311), and to have a length at least equal to the length of the feed plungers (110, 210, 310, 510);
m) the rod (350) to be cogged on the side facing the cartridge head (105, 205, 305, 505);
n) the cross-section of the rod (350) to be smaller than the cross-section of the internal hollow cylinder or of the internal irregularly- or regularly-shaped hollow body;
o) the internal hollow cylinder and the cartridges (101, 201, 301, 501) to be connected up to half of their length through at least one slit (358) having a cross-section that is smaller than the cross-section of the fin (111, 211, 311) or fins (111, 211, 311); and
p) a flexible snap-in device (358) having a cross-section smaller than or equal to that of the cogged rod (350) to be arranged on the end of the hollow cylinder or of the internal irregularly- or regularly-shaped hollow body on the side facing the cartridge floor (109, 209, 309, 509).

A method for closing the cartridge system is characterised in that the dispensing tube (240) is rotated by its dispensing tube tip (242) opposite to the cartridge head (5, 105, 205, 305, 505) or cartridge heads (5, 105, 205, 305, 505) in a manner such that the openings of the rotatable cylinder (20, 120, 220, 320, 420, 520) are not situated over the opening or openings (12, 112, 212, 312, 512) of the cartridge head (5, 105, 205, 305, 505) or cartridge heads (5, 105, 205, 305, 505).

A method for opening the cartridge system according to the invention is characterised in that the dispensing tube (240), which is situated opposite to the direction of the cartridge head (5, 105, 205, 305, 505) or cartridge heads (5, 105, 205, 305, 505), is rotated by its dispensing tube tip (242) in the direction of the cartridge head (5, 105, 205, 305, 505) until the dispensing tube (240) is perpendicular or approximately perpendicular to the axis or axes of the cartridge (1, 101, 201, 301, 501) or cartridges (1, 101, 201, 301, 501) and the dispensing tube tip (242) is oriented opposite to the cartridge head (5, 105, 205, 305, 505) or cartridge heads (5, 105, 205, 305, 505), whereby the openings of the rotatable cylinder (20, 120, 220, 320, 420, 520) become situated above the openings (12, 112, 212, 312, 512) of the cartridge head (5, 105, 205, 305, 505) or cartridge heads (5, 105, 205, 305, 505) and thereby form at least one connection that is permeable for pasty materials.

The cartridge systems according to the invention are suitable for temporary closure of one-component cartridge systems and multi-component cartridge systems.

The cartridge system according to the invention can be used for temporary storage and subsequent application of paste-like adhesives, sealants, food items, medicinal products, dental materials, inorganic bone cements, and polymethacrylate bone cements.

The features of the invention disclosed in the preceding description and in the claims, figures, and exemplary embodiments, can be essential for the implementation of the various embodiments of the invention both alone and in any combination.

List of reference numbers

| | |
|---|---|
| 1, 101, 201, 301, 501 | Cartridge |
| 3, 103, 203, 303, 503 | Cartridge wall |
| 5, 105, 205, 305, 505 | Cartridge head |
| 9, 109, 209, 309, 509 | Cartridge floor |
| 10, 110, 210, 310, 510 | Feed plunger |
| 111, 211, 311 | Fin |
| 12, 112, 212, 312, 512 | Opening |
| 20, 120, 220, 320, 420, 520 | Valve/cylinder |
| 22, 122, 222, 322, 522 | Bracket/bearing |
| 24, 124, 224, 324, 424 | Connector |
| 26, 126, 226, 326, 426 | Outlet opening |
| 28, 128, 228, 328, 428 | Fastening means/thread |
| 30, 130, 230, 330, 430, 530 | Passage |
| 240 | Dispensing tube |
| 242 | Dispensing tube tip |
| 244 | Fastening means |
| 246 | Mixer |
| 350 | Rod |
| 352 | Snap-in locking means |
| 354 | Opposite snap-in locking means |
| 356 | Fin |
| 358 | Slit |
| A | Rotation axis |

What is claimed:

1. A cartridge system for application of a material, the cartridge system comprising:
at least two cartridges, each cartridge has cartridge walls and a cartridge head having at least one opening in each cartridge head;
wherein the cartridge walls of each of the at least two cartridges are separated by an open space;
wherein the system further comprises a bracket arranged on the cartridge heads of the at least two cartridges;
wherein a valve is mounted in rotatable manner in the bracket;
wherein the valve comprises at least one passage through the valve that is connected to an outlet opening of the valve;
wherein the valve, when located in the closed position, closes the at least one opening in each cartridge head of the at least two cartridges in a sealed manner;
wherein the at least one passage of the valve is connectable to the at least one opening in each cartridge head of the at least two cartridges when the valve is located in an open position such that the cartridge content of the at least two cartridges is squeezable out of the at least two cartridges through the outlet opening of the valve;
wherein the valve is movable from the closed position to the open position through a rotation of the valve;
wherein the system further comprises a dispensing tube is arranged on the valve such that, when the valve is in the closed position, the dispensing tube is located in the open space between the at least two cartridges, and is substantially parallel to the at least two cartridges.

2. The cartridge system according to claim 1, wherein each cartridge comprises at least one feed plunger opposite from each cartridge head for expelling the cartridge content through the opening of each cartridge head, wherein each feed plunger closes the each cartridge on a floor side of the at least two cartridges.

3. The cartridge system according to claim 2, wherein a rod is arranged parallel to the at least two cartridges, wherein the rod comprises a snap-in locking means on a side facing the valve, and an opposite snap-in locking means is attached at the cartridge walls and acts with the snap-in locking means of the rod in a manner such that a motion of the rod in the direction of the cartridge floor and a motion of the feed plungers out of the cartridges is hampered or prevented.

4. The cartridge system according to claim 3, wherein the rod is arranged between the at least two cartridges.

5. The cartridge system according to claim 3, wherein the rod is arrange in the open space formed between the at least two.

6. The cartridge system according to claim 3, wherein the rod is arranged parallel to the feed plungers and fixedly connected to the feed plungers through at least one fin or plate.

7. The cartridge system according to claim 1, wherein the valve is configured such that, with the valve located in the open position, at least one fluid-tight connection from the at least one opening in each cartridge head to the at least one passage of the valve is provided.

8. The cartridge system according to claim 1, wherein a connector is arranged on the valve, wherein the connector comprises a fastening means for fastening the dispensing tube, the passage of the valve extends through the connector, and the outlet opening of the valve is arranged on the connector.

9. The cartridge system according to claim 8, wherein the fastening means is an external thread.

10. The cartridge system according to claim 8, wherein the dispensing tube comprises a fastening means through which the dispensing tube is connected to the fastening means of the connector in a detachable manner or through which the dispensing tube is connected to the valve in a fixed manner.

11. The cartridge system according to claim 1, wherein the dispensing tube commences on the outlet opening of the valve and extends the passage to a dispensing tube tip.

12. The cartridge system according to claim 1, wherein the dispensing tube comprises a static mixer.

13. The cartridge system according to claim 1, wherein the valve, located in the open position or in the closed position, is arranged in a press-fit manner over the at least one opening in each cartridge head and closes the at least one opening in each cartridge head in a sealed manner when the valve is located in the closed position or connects the at least one opening in each cartridge head in a sealed manner to the passage of the valve when the valve is located in the open position.

14. The cartridge system according to claim 1, wherein the at least two cartridges are arranged to be parallel with respect to each other.

15. The cartridge system according to claim 14, wherein the at least one passage in the valve connects the openings of the at least two cartridges to the outlet opening of the valve when the valve is located in the open position.

16. The cartridge system according to claim 1, wherein the valve is cylinder-shaped, or takes a shape of a cylinder with an elliptical base or a shape of a section of a cylinder.

17. The cartridge system according to claim 1, wherein the material is medical cement.

18. The cartridge system according to claim 1, wherein the dispensing tube is arranged parallel with respect to the at least two cartridges when the valve is located in the open position.

* * * * *